United States Patent
Wang et al.

(10) Patent No.: US 8,137,735 B2
(45) Date of Patent: Mar. 20, 2012

(54) ELASTOMERIC ARTICLE WITH ANTIMICROBIAL COATING

(75) Inventors: Shiping Wang, Libertyville, IL (US); Ida Berger, Buffalo Grove, IL (US)

(73) Assignee: Allegiance Corporation, McGaw Park, IL (US)

( * ) Notice: Subject to any disclaimer, the term of this patent is extended or adjusted under 35 U.S.C. 154(b) by 332 days.

(21) Appl. No.: 11/271,666

(22) Filed: Nov. 10, 2005

(65) Prior Publication Data

US 2007/0104766 A1    May 10, 2007

(51) Int. Cl.
*A41D 19/00* (2006.01)
*C09D 191/08* (2006.01)

(52) U.S. Cl. .................... 427/2.3; 106/18.29; 223/78

(58) Field of Classification Search ............... 106/18.29; 223/78; 427/2.3
See application file for complete search history.

(56) References Cited

U.S. PATENT DOCUMENTS

| | | | |
|---|---|---|---|
| 4,499,154 A * | 2/1985 | James et al. | 428/494 |
| 5,272,012 A | 12/1993 | Opolski | |
| 5,357,636 A * | 10/1994 | Dresdner et al. | 2/161.7 |
| 5,741,828 A | 4/1998 | Stoy et al. | |
| 6,012,169 A * | 1/2000 | Nishi et al. | 2/161.7 |
| 6,378,137 B1 * | 4/2002 | Hassan et al. | 2/161.7 |
| 6,709,725 B1 * | 3/2004 | Lai et al. | 428/36.8 |
| 2004/0010077 A1 | 1/2004 | Nile et al. | |
| 2005/0112180 A1 * | 5/2005 | Chou | 424/443 |
| 2005/0186258 A1 * | 8/2005 | Wang et al. | 424/443 |
| 2005/0196358 A1 | 9/2005 | Georgiades et al. | |

FOREIGN PATENT DOCUMENTS

| | | |
|---|---|---|
| EP | 0 300 814 A2 | 1/1989 |
| EP | 0 328 421 A2 | 8/1989 |
| WO | WO 01/43788 A2 | 6/2001 |

OTHER PUBLICATIONS

International Search Report for PCT/US2006/043620 completed on Apr. 11, 2007 and mailed on Apr. 23, 2007.

* cited by examiner

*Primary Examiner* — Karlheinz R Skowronek
*Assistant Examiner* — Ali Soroush
(74) *Attorney, Agent, or Firm* — Arent Fox LLP

(57) ABSTRACT

A first aspect of the present invention is directed to a surface treatment for elastomeric articles such as medical gloves, comprising a water-based coating formulation and antimicrobial agent(s) embraced therein in an essentially powder-free composition coating. A second aspect of the present invention is directed to a water-based coating formulation for elastomeric articles such as gloves comprising at least one non-volatile water-soluble antimicrobial agent in a controlled-release matrix comprising a blend of a hydrophilic polymer and a hydrophobic component. The controlled-release matrix/blend requirements include: compatibility with the antimicrobial agent, formation of a reservoir of antimicrobial agent, coating film flexibility and lower water-solubility than the antimicrobial agent. A third aspect of the present invention is directed to a method for treating medical gloves comprising dipping, spraying, tumbling or other means for applying to the glove surface a composition to provide medical gloves with sustainable antimicrobial activity.

20 Claims, No Drawings

ELASTOMERIC ARTICLE WITH ANTIMICROBIAL COATING

BACKGROUND OF THE INVENTION

The present invention relates to elastomeric articles such as gloves with an antimicrobial coating, which allows the articles to maintain a high efficacy of antimicrobial activity. Gloves according to the invention are particularly, but not exclusively, useful for medical applications, for example as both exam and surgical gloves. Medical gloves according to the invention exhibit good "time-kill" activity against a broad spectrum of microorganisms and maintain their antimicrobial activity after being stored and transported under warm and humid environments. The invention may alternatively have applications in other skin protection environments including, but not limited to, food-contact gloves, dental gloves, industrial gloves, laboratory gloves, and other medical devices such as catheters, protective covers and tubes.

Gloves have become an everyday part of clinical practice for healthcare workers and function as an element of personal protective equipment, which safeguard both the glove wearer and the patient from infection. Hospital acquired infection can be further reduced by compliance With hand washing and glove isolation procedures. Even though the glove protects the individual wearing the glove, cross-contamination may still occur, i.e., patient-to-patient, surface-to-surface and surface-to-patient. For example, the surface of a glove can become contaminated after being in contact with bodily fluids that contain infectious microbes. These microbes can grow on the surface of the glove and eventually be transferred to another person or surface.

To address the problem of infection and cross-contamination, efforts are underway to develop antimicrobial gloves. An antimicrobial glove requires that a glove surface have "quick-kill" properties, i.e., microorganisms are killed on contact with the glove surface. Treating a glove surface with non-volatile water-soluble antimicrobial agents is one approach to meeting the "quick-kill requirement" and cationic bis-biguanide and quaternary ammonium salt are two types of effective antiseptic/disinfectant agents. Chlorhexidine digluconate (CHG) and benzalkonium chloride (BKC) are acceptable examples of these types of agents, respectively.

However, an unresolved problem for developing effective antimicrobial gloves is the difficulty of maintaining the antimicrobial efficacy following production. Glove products are made of either thermosets such as natural rubber and synthetic rubber, including nitrile rubber or thermoplastics such as styrene-type block copolymers and polyurethanes. These elastomeric products possess excellent mechanical properties such as deformation resistance but they can be also be sensitive to liquid or moisture permeation, swelling or absorption. The degree of glove-liquid interaction depends upon the type of elastomers and the chemical nature of the penetrants. Antimicrobial agents coated on the glove surface are not chemically bound to the surface and tend to migrate into the glove substrate when moisture is absorbed by the glove surface. This type of moisture absorption takes place during glove storage. The moisture provides a vehicle for the diffusion of the antimicrobial agent into the body of the glove. As a result, when gloves are finally ready for use in a hospital setting, the availability of antimicrobial agents on the glove surface can be significantly reduced and antimicrobial efficacy can be compromised by virtue of migration of the antimicrobial agent away from the surface and into the glove itself. The loss of antimicrobial agent from the glove surface during storage is accentuated in warm and/or humid environments.

Previous attempts to preserve antimicrobial efficacy tried to localize and fix the antimicrobial agent on the surface of the glove and include the use of starch powders on the surface of the treated gloves. For example, U.S. Pat. No. 5,089,205 requires the presence of starch powder as a carrier for an antimicrobial agent. In addition, U.S. Pat. No. 5,492,692 describes a high-energy co-precipitate powder of polyvinylpyrrolidone/iodine and an anti-HIV agent such as Nonoxynol-9 as a powder coating on elastomeric articles. However, the disclosures discussed above do not provide essentially powder-free gloves and other elastomeric articles with sustainable, broad-spectrum antimicrobial activity. U.S. Pat. Publication No. 2005/0186258 describes a coating on elastomeric articles consisting of CHG, BKC and a moisture resistant package, which maintained antimicrobial activity after aging at 40° C./70% relative humidity. This patent does not provide the elastomeric articles with sustainable antimicrobial activities.

The phrase "sustainable, broad-spectrum antimicrobial activity" as used herein refers to two properties. In one embodiment, the phrase refers to an elastomeric article such as a glove, which retains its antimicrobial activity for a long shelf life as defined in ASTM D 7160-05. In another embodiment, the phrase refers to an elastomeric article such as a glove which maintains its broad-spectrum antimicrobial activity after its packaging is opened, which normally spans an extended period of time i.e., no less than about one week under ambient conditions. Broad-spectrum refers without limitation to gram-positive bacteria such as *Staphylococcus aureus* and *Enterococcus faecalis*, and Gram negative bacteria such as *Escherichia coli* and *Pseudomonas aerignosa*, and clinical isolates such as methicillin-resistant *Staphylococcus aureus* (MRSA) and vancomycin-resistant *Enterococcus faecium* (VRE). The above bacteria can be found in a hospital environment.

Therefore, there is a need for powder-free medical gloves and other elastomeric articles, which exhibit effective and sustainable antimicrobial activity against a broad-spectrum of microorganisms.

One objective of the invention is to develop elastomeric articles such as medical gloves with a surface treatment having sustainable antimicrobial properties, i.e., maintain quick-kill activity against microbes, even after an extended period of time, i.e., no less than about one week under ambient conditions without sacrificing other properties. The sustainability can be determined using accelerated age testing, where gloves are subjected to elevated temperatures for a given length of time (7 days at 70° C., ASTM D 6319-00a$^{e3}$, Test Method D 573). Another objective of the invention is to develop a novel surface coating formulation which can protect an antimicrobial agent from loss of activity due to the presence of moisture, which enhances migration of the antimicrobial agent into the body of the glove over time. An additional objective of the invention is to develop a processing method, glove coating treatment and glove packaging for manufacturing sustainable antimicrobial elastomeric articles such as medical gloves.

SUMMARY OF THE INVENTION

A first aspect of the present invention is directed to a surface treatment for elastomeric articles such as medical gloves, comprising a water-based coating formulation and antimicrobial agent(s) embraced therein in an essentially powder-free composition coating.

A second aspect of the present invention is directed to a water-based coating formulation for elastomeric articles such as gloves comprising at least one non-volatile water-soluble antimicrobial agent in a controlled-release matrix comprising a blend of a hydrophilic polymer and a hydrophobic component. The controlled-release matrix/blend requirements include: compatibility with the antimicrobial agent, formation of a reservoir of antimicrobial agent, coating film flexibility and lower water-solubility than the antimicrobial agent.

A third aspect of the present invention is directed to a method for treating medical gloves comprising dipping, spraying, tumbling or other means for applying to the glove surface a composition to provide medical gloves with sustainable antimicrobial activity.

DETAILED DESCRIPTION OF THE INVENTION

Articles according to the invention comprise an elastomeric substrate with an essentially powder-free coating with sustainable antimicrobial activity, where the coating comprises a controlled-release matrix comprising a blend of a hydrophilic polymer and a hydrophobic component, and at least one non-volatile water-soluble antimicrobial agent.

The phrase "sustainable, broad-spectrum antimicrobial activity" as used herein refers to two properties. In one embodiment, the phrase refers to an elastomeric article such as a glove, which retains its antimicrobial activity for a long shelf life, as defined in ASTM D 7160-05. In another embodiment, the phrase refers to an elastomeric article such as a glove which maintains its broad-spectrum antimicrobial activity after its packaging is opened to the atmosphere, which normally spans an extended period of time, i.e., no less than about one week under ambient conditions. Broad-spectrum refers without limitation to gram positive bacteria such as *Staphylococcus aureus* and *Enterococcus faecalis* and Gram negative bacteria such as *Escherichia coli* and *Pseudomonas aerignosa*, and clinical isolates such as methicillin-resistant *Staphylococcus aureus* (MRSA) and vancomycin-resistant *Enterococcus faecium* (VRE). The above bacteria can be found in a hospital environment.

By "powder-free" is meant an elastomeric glove that has little or no powder or starch. According to ASTM D 6124-01, the glove must have less than about 2 mg of powder or "any water insoluble, filter retained residue" per glove.

The type of elastomeric article of the invention is not limited but can be a glove, a condom, a stent, a catheter balloon, a probe cover or another elastomeric device. In the case of medical or industrial gloves, preferably the gloves are made of a natural rubber latex, nitrile, polychloroprene, polybutadiene, polyvinylchloride (PVC), polyurethane, polyisoprene, styrene type block copolymers or other synthetic elastomers, including blends thereof and any modification thereof.

Gloves according to the invention can be a single-layer or contain more than one layer in a laminate fashion. Additionally, gloves can contain standard fillers and additives. Some glove making materials that can serve as starting materials for surface modification include those described in U.S. Pat. No. 6,391,409, and U.S. Pat. No. 6,195,805. For example, U.S. Pat. No. 6,391,409 describes powder-free nitrile coated gloves with an intermediate rubber-nitrile layer between the glove and the coating. Additionally, U.S. Pat. No. 6,195,805 describes powder-free surgical gloves. The above patents are incorporated by reference in their entirety.

Non-volatile, water-soluble antimicrobial agents include natural components including botanical compounds such as aloe, acids such as anisic acid, hydroxy acids such as lactic acid, polypeptides such as N-cocoyl-L-arginine ethyl ether DL-pyrrolidone carboxylate CAE, enzymes such as lactoperoxidase, polysaccharides such as chitosan and proteins such as ionic lysostaphin; synthetic components including metal salts such as copper acetate and silver sulfadiazine, phenol derivatives such as phenoxyethanol, sulfur-containing compounds such as mafenide acetate, surfactants such as Nonoxynol-9, aminoglycosides such as streptomycin, iodine complexes such as povidone-iodine, hydric solvents such as benzyl alcohol, alkyl guanidines such as dodecylguanidine hydrochloride (DGH), anionic polymers such as polystyrene sulfonate, cationic polymers such as polytrimethoxysilyl propyldimethyloctadecyl ammonium chloride (AEM 5700™) and cationic nitrogen-containing organic compounds such as bis-biguanide salts and quaternary ammonium salts such as poly[(dimethylimino)-2-butene-1,4-diylchloride] and [4-tris (2-hydroxyethyl)ammonio]-2-butenyl-w-[tris(2-hydroxyethyl)ammonio]dichloride available as Polyquaternium-1.

Bis-biguanide salts include hexamethylene biguanide hydrochloride (available as Vantocil IB®), polyhexamethylene biguanide hydrochloride (also known as PHMB, available as Cosmocil CQ®), bis-biguanide alkanes and mixture of thereof. A preferred bis-biguanide salt is 1,1'-hexamethylene bis(5-(p-chlorophenyl)biguanide salt commonly known as chlorhexidine salt. This form includes chlorhexidine diacetate, chlorhexidine dihydrochloride, chlorhexidine diphosphanilate or chlorhexidine digluconate, mainly differing by their solubility profile in various solvents and their application. The most preferred chlorhexidine salt according to the invention is chlorhexidine digluconate, i.e., chlorhexidine gluconate (CHG). The CHG can be present in an amount ranging from about 0.5% to about 85% by weight of total solids, more preferably from about 1.0% to about 75.0% by weight of total solids, and most preferably about 5.0% to about 60.0% by weight of total solids.

Water-soluble quaternary ammonium salts include benzalkonium chloride (BKC), chloroallyl hexaminium chloride, benzethonium chloride, methylbenzethonium chloride, cetyl trimethyl ammonium bromide, didecyldimethyl ammonium chloride, cetyl pyridinium chloride (CPC), dioctyldimethyl ammonium chloride and mixtures thereof. A preferred water-soluble quaternary ammonium salt is benzalkonium chloride (BKC). The BKC can be present in an amount ranging from about 0.0% to about 80.0% by weight of total solids, in a more preferred amount ranging from about 0.0% to about 75.0% by weight of total solids, and most preferably in an amount ranging from about 0.0% to about 33.0% by weight of total solids.

The term "hydrophilic polymer" as used herein refers to polymers or copolymers that can be water-soluble or water-dispersible; anionic, cationic, or nonionic; and crosslinked or not cross-linked. They generally include polar groups such as hydroxyl, amide, amine or ether groups, and other groups with a high affinity for water. In addition, they should provide good adhesive, binding, film-forming and water-swelling properties. No particular limitation is imposed on hydrophilic polymers or copolymers useful in the practice of the present invention. However, specific examples thereof include the following:

natural polymers: collagen, chitosan, gum, carrageenan, pullulan, pectin, dextrin, quince, hyaluronic acid, chondroitin sulfate, methyl polyglutamate, sodium alginate and cellulosic polymers such as: cationized cellulose, carboxymethyl cellulose, hydroxyethyl cellulose, and hydroxypropyl methyl cellulose;

acrylic polymers: polyacrylic acid, polymethylacrylic acid, polyalkyl acrylic acid, polyalkylmethacrylic acid, polyhydroxyalkyl methacrylic acid, polyalkoxyalkyl acrylate, polyalkoxyalkyl methacrylate, polyalkoxy acrylamide, polyacrylamide and blends thereof, copolymer or salts thereof;

carboxyvinyl polymers: polyvinyl caprolactam, olefin-maleic anhydride copolymer, isobutylene-sodium maleic anhydride copolymer, ethylene-maleic anhydride copolymer, and salts thereof or blends thereof;

vinylpyrrolidone(VP)-based polymers: polyvinylpyrrolidone (PVP), VP-styrene copolymer, VP-vinyl acetate copolymer, and diethyl sulfate VP-dimethylaminoethyl-methacrylic acid copolymer, and blends thereof;

amphoteric polymers: polymethacryloyloxyethyltrimethyl ammonium chloride, alkyl vinyl ether maleic anhydride (AVE/MA) copolymer, poly-2-aminopropyl acrylate, poly (diethylaminoethyl methacrylate), copolymers such as dimethylaminoethyl methacrylate copolymer and zwitterionic polymers such as polybetaines such as poly-2-ethynyl-N-(4-sulfobutyl)pyridinium betaine (PESPB), polysulfobetaines such as poly-N,N-dimethyl-N-3-sulfopropyl-3'methacrylamidopropanaminium and copolymers such as diallyldimethylammonium chloride-maleamic acid copolymers; and other polymers: polyvinyl methyl ether, toluene sulfonamide polymer, polyurethane, polyamide-epichlorohydrin-resin, polyethylene-imine, polyethylene glycol, ethylene-vinyl acetate copolymer and ethylene-vinyl alcohol copolymer.

Among the above-mentioned hydrophilic polymers, acrylic polymers are suitable hydrophilic polymers for application of the present invention. Preferred acrylic polymers include cationic dimethyl aminoalkyl based polymers (e.g. polyquaternium polymers), cationic acrylic copolymers which can be crosslinked polyacrylic acid (e.g. Carbopol® polymers), crosslinked hydroxyalkyl acrylate copolymer (e.g. hydrogel polymers) and neutralized and non-neutralized anionic acrylic polymers.

Preferred hydrophilic polymers are cationic acrylic copolymers which include Polycat® M-30, Nalkat® 8108, Aquamere®, and Eudragit®. Eudragit® RS 30D is most preferred, which is a pH-independent aqueous copolymer of ethyl acrylate and methyl methacrylate with quaternary ammonium groups. The pendant-cationic, ammonium groups of acrylic polymers provide water-permeability to resulting films. The hydrophilic polymer can be present in an amount ranging from about 0.5% to about 99.0% by weight of total solids, more preferably present in an amount ranging from about 1.0% to about 75.0% by weight of total solids weight, and most preferably present in an amount ranging from about 2.0% to about 60.0% by weight of total solids.

The hydrophobic component herein refers to low or medium molecular weight materials which have water resistance and facilitate film-formation of a high molecular weight hydrophilic polymer through inter-molecular lubrication. No particular limitation is imposed on the hydrophobic component useful in the practice of the present invention. However, specific examples thereof include the following:

Natural components such as gum rosin, modified natural components such as hydrogenated caster oil, vegetable proteins such as soy protein, animal components such as shellac, non-volatile coalescing solvent such as polybutylene, waxy compound such as hydrocarbons, cellulose derivatives such as methyl cellulose, oligomeric polyolefins such as polyethylene and plasticizers such as magnesium stearate, dibutyl phthalate, diethyl phthalate, and tributyl citrate.

Preferred examples of the hydrophobic component used in the coating formulation of the present invention are waxy compounds such as a wax dispersion. Wax dispersions include, but are not limited to, dispersions of: paraffin wax, synthetic wax, polyethylene wax, oxidized polyethylene wax, ethylene acrylic acid copolymer (EAA) wax, ethylene vinylacetate copolymer wax, silicone wax, fluoroethylene wax, carnauba wax, Fischer-Tropsch wax, ester wax, and combinations thereof.

Paraffin wax is a preferred hydrophobic component. Paraffin wax is a saturated hydrocarbon derived from petroleum with chain length of about 25-30 carbons, which is used for hydrophobicity enhancement, friction control, anti-blocking and barrier properties. The performance of paraffin waxes is entirely dependent on the type of petroleum, formulation conditions, chain length and application in the final product. Anionic, cationic, amphoteric or nonionic stabilizers can be used to disperse paraffin wax in an aqueous carrier. Non-ionic paraffin wax dispersions are preferred, such as Michem® Lube 743 (ML 743) of Michelman Inc., Aquacer 498® of BYK-Cera and NF emulsifying wax of Koster Keunen. The hydrophobic wax can be present in an amount ranging from about 0.5% to about 99.0% by weight of total solids, more preferably in amount ranging from about 1.0% to about 55% by weight of total solid, and most preferably present in an amount ranging from about 1.5% to about 40% by weight of total solids.

In addition, the coating formulation also contains other ingredients, which include optional beneficial agents for the skin and additional agents such as wetting agents and antifoam agents, provided that the antimicrobial property of the treated article is not compromised.

A wetting agent is an example of a functional additive which improves coating film quality by providing quick spreading and uniform coverage of the coating formulation. Wetting components are known in the art and may include nonionic polyether dimethylpolysiloxane dispersions such as BYK-348 of BYK Chemie. Antifoam agents suppress foam forming during the formulation process and coating application, improving the dried coating quality. They can include anionic and nonionic materials such as ethylene glycol diols, sulfate surfactants, phosphate esters, polyethylene glycol, silicone-based compositions and others. Ethylene glycol diols such as Surfynol® TG of Air Product Chemical is a preferred antifoaming agent.

While maintaining antimicrobial efficacy, the coating formulation of the invention used for surface-treatment of gloves may also contain optional skin-benefit agents. Such optional agents include humectants, skin conditioners, antioxidants, fragrance and others. Again, the inclusion of these agents should not interfere with the formulation, processing and antimicrobial efficacy of the coated article.

The invention encompasses the application of an antimicrobial coating composition to any desired surface of an elastomeric article. A preferred embodiment according to the invention is prepared by applying the antimicrobial coating composition to the outer surface of a medical or an industrial glove to minimize or reduce cross-contamination as a result of multiple contacts. By outside surface is meant the portion of the glove that comes into contact with other objects such as patients, medical instruments, tabletops or counters. The antimicrobial composition of this invention can also be applied to the inside surface of a surgical glove to inhibit any significant growth of microorganisms. By inside surface is meant the surface that comes into contact with the wearer's hand.

Surprisingly, the inventors have found that a blend of the invention comprising a hydrophilic polymer (cationic acrylic copolymer) and a hydrophobic component (paraffin wax) provides good film-forming properties and the controlled-release of an antimicrobial agent embraced therein. Individually, the hydrophilic polymer Eudragit® RS 30D is a brittle resin and paraffin wax ML 743 is incapable of forming a film. Their glass transition temperatures are higher than room temperature ($T_g$ of Eudragit® RS 30D=50° C.; $T_g$ of ML 743=61-66° C.). However, the blend of Eudragit® RS 30D and ML 743 forms a flexible, non-brittle film coating on a glove surface after a 70° C. curing process. In a dried film made of a blend comprising Eudragit® RS 30D and paraffin wax, the paraffin wax softens the cationic acrylic polymer film, and provides increased hydrophobicity to the polymer film resulting in increased water resistance and moisture barrier properties.

Both CHG and BKC are non-volatile water-soluble antimicrobial agents that uniformly distribute within a coating film made by a blend of Eudragit® RS 30D and paraffin wax ML 743. When applied to a glove, the coating film not only protects CHG and BKC from excessive loss, but also provides controlled-release of the antimicrobial agent on to the glove surface against a broad spectrum of microorganisms: Gram positive bacteria such as *Staphylococcus aureus* and *Enterococcus faecalis*, and Gram negative bacteria such as *Escherichia coli* and *Pseudomonas aerignosa*, and clinical isolates such as methicillin-resistant *Staphylococcus aureus* (MRSA) and vancomycin-resistant *Enterococcus faecium* (VRE). These bacteria can be found in a hospital environment.

While not wishing to be bound by theory, the inventors believe that the hydrophilic polymer such as a cationic acrylic copolymer (e.g. Eudragit® RS 30D) provides a reservoir for water soluble antimicrobial agents such as CHG and BKC and the hydrophobic component such as a paraffin wax (e.g. Michem® Lube 743) improves the film's flexibility through its plasticizing effect. The balance of the hydrophobicity-hydrophilicity of the hydrophilic polymer and hydrophobic component in the coating film can control the release of an antimicrobial agent such as CHG.

The coating composition of the invention can be applied to the glove surfaces using conventional equipment and techniques readily available to those in the field of manufacturing elastomeric articles, including on-line and off-line techniques such as dipping, spraying, tumbling and the like. Examples of coating techniques, are described in U.S. Pat. Pub. No. 2004/0126604 and U.S. Pat. Pub. No. 2004/0241201. For preparing surgical gloves, a preferred method of application is off-line spraying. For the preparation of examination gloves, a preferred on-line method of application is dip coating, and a preferred off-line method is the tumbling method of coating.

The most preferred embodiment for the water-based formulation is the combination of a hydrophilic polymer, hydrophobic component and antimicrobial agent. In the most preferred embodiment, CHG can be present in an amount ranging from about 5.0% to about 60.0% by weight of total solids, BKC can be present in an amount ranging from more than about 0.0% to about 33.0% by weight of total solids, hydrophilic polymer can be present in an amount ranging from about 2.0% to about 60.0% by weight of total solids, hydrophobic component can be present in an amount ranging from about 1.5% to about 40.0% by weight of total solids. The dry coating weight for the glove is between about 1 to about 200 mg/glove, more preferably between about 20 to about 100 mg/glove, and most preferably between about 30 to about 70 mg/glove.

A moisture-resistant package enhances the availability of antimicrobial agent on a glove surface, which improves glove quick-kill. Package material, desiccant and pouch design used for a glove according to the invention can vary, while the amount of desiccant can depend on the number of gloves being packed. For example, packaging can be achieved in a moisture-resistant, aluminum/nylon laminate pouch with desiccant. Without wishing to be bound by theory, it is believed that a preferred packaging system maintains low humidity in the vicinity of the glove and ensures less diffusion of antimicrobial agent into the glove body resulting in a high efficacy of glove antimicrobial activity. Using these conditions, a quick-kill improvement of 1-log reduction on a five-minute exposure time is preferred, a 2-log reduction on a five-minute exposure time is more preferred, and at least a 2-log reduction after a one-minute exposure time is most preferred. A preferred relative humidity for the inside of a glove package is below about 40%, more preferably below about 30%, and most preferably below about 10% or below about 5%.

According to the present invention, treated gloves can be stored in an air-conditioned room before being packed. Storage time can be kept within a few days and packaging can be carried out under low humidity and ambient temperature with a complete seal for the packaging.

General Experimental Measurements and Test

Glove Aging: Sustainability is the ability of a product to maintain a particular level of functionality over an extended period of time, such as product shelf life as defined in ASTM D7160-05. The sustainability of a glove according to the invention can be determined using accelerated age testing, where gloves are subjected to elevated temperatures for a given length of time. An example of an accelerated aging test (7 days at 70° C.) for glove shelf life study is documented in ASTM D 6319-00a$^{e3}$, Test Method D 573.

In these experiments, gloves were packed in a 12.0×6.5 inch pouch with desiccant bags and a Smart Reader (ACR Systems Inc., Surrey, British Columbia) humidity recorder was inserted in the pouch.

Dry Coating Weight (DCW): The rate of release of antimicrobial agent from a coating is related to the coating thickness. The coating thickness is regulated by the dry coating weight, i.e., the amount of coating deposited on the glove.

The dry coating weight in this study was determined gravimetrically. First, the combined weight of ten untreated gloves of each type was measured, $W_a$. Next, gloves were prepared as described in the examples and then ten gloves were weighed, $W_b$. The calculation is: dry coating weight=$(W_b-W_a)/10$ gloves, in mg/glove. Due to glove size variation (small, medium and large), measured dry coating weight per glove is presented as medium size by normalizing glove weight.

Antimicrobial Agent Measurement by HPLC: The overall and surface concentrations of antimicrobial agent were determined using HPLC. Tests were conducted using a Waters HPLC system and YMC-Pack™ ODS-AM column (5µm, 120 Å, 150×6.0 mm I.D., Waters Corporation).

TABLE 1

| Materials | |
| --- | --- |
| Ingredient | Manufacturer/Location |
| Acetonitrile (HPLC Grade) | Honeywell, Burdick and Jackson/Muskegon, MI |
| Water (HPLC Grade) | Honeywell, Burdick and Jackson/Muskegon, MI |
| Ammonium Thiocyanate | Aldrich Chemical Co./Milwaukee, WI |
| Methanol (HPLC Grade) | Honeywell, Burdick and Jackson/Muskegon, MI |
| Trifluoroacetic Acid | Aldrich Chemical Co./Milwaukee, WI |

Two types of extractions were conducted on the glove, one with methanol (which provides the overall concentration of antimicrobial agent on and in the glove) and the other with water (which provides the surface concentration of antimicrobial agent on the glove). The antimicrobial components are soluble in both methanol and water. Methanol is able to penetrate into the glove body, removing all antimicrobial agent, that which has migrated into the glove along with any that is coated on the surface. Water cannot penetrate into the glove body and only removes antimicrobial agents coated on the surface of the glove. For BKC, the method required an acetonitrile/water/ammonium thiocyanate eluent (70%/30%/0.5%, v/v/w), 1 mL/min flow rate, and an injection volume of 50 µL (detection at 260 nm, 0.02 AUFS). For CHG, the method required an acetonitrile/water/trifluoroacetic acid eluent (30%/70%/0.1%, v/v), a flow rate of 1 mL/min, and an injection volume of 10 µL (detection at 219 nm, 0.10 AUFS). Extractions were conducted on gloves before and after aging. The coating concentrations for the control glove, Sample 1-1 (containing only antimicrobial agents), are set forth in the following Table 2:

| Sample 1-1 | Coating Concentration (mg/glove) | | | |
|---|---|---|---|---|
| | Water Extraction | | Methanol Extraction | |
| (control) | BKC | CHG | BKC | CHG |
| Before Age | 1.2 ± 0.1 | 4.4 ± 0.8 | 6.7 ± 0.3 | 8.0 ± 1.0 |
| After Age | <0.02 | 0.17 ± 0.03 | N/A | N/A |

Antimicrobial Activity: A test method was developed in order to evaluate the antimicrobial efficacy of the gloves. The method included applying a microbial suspension on the active glove surface, maintaining contact for a designated time interval, extracting the surviving cells in neutralizing agent solution, incubating the extracted inoculum and quantifying the microbe level to determine a log reduction from the initial inoculum titer. All the materials used were from ATCC (American Type Culture Collection). Reference strains were used for all tests:

| Microorganism | ATCC # |
|---|---|
| *Escherichia coli* Gram-negative bacteria | 11229 |
| *Enterococcus faecalis* Gram-positive bacteria | 29212 |
| *Staphylococcus aureus* Gram-positive bacteria | 6538 |
| *Staphylococcus epidermidis* Gram- positive bacteria | 12228 |
| *Pseudomonas Aeruginosa* Gram-negative bacteria | 15442 |
| *Enterococcus faecium*, VRE Clinical Isolate | 51559 |
| *Staphylococcus aureus*, MRSA Clinical Isolate | 43300 |

The microbial suspension was prepared using the Direct Colony Suspension Method in sterile saline (Reference: *Methods for Dilution Antimicrobial Susceptibility Tests for Bacteria That Grow Aerobically*; Standard: M7-A6. Clinical and Laboratory Standards Institute).

The initial inoculum titer determines the level of the challenge microbial suspension. An aliquot of 0.02 ml of the microbial suspension was added to 10 ml neutralizing solution. The solution was enumerated by the traditional bacteriological techniques using standard agar plating methods.

The effectiveness of the glove's antimicrobial activity was measured via log reduction from the initial inoculum titer. Testing glove samples were aseptically cut from the palm areas to approximately 1 square inch. An aliquot of 0.02 ml of microbial suspension was applied on a sterile micro cover glass (18×18 mm) and placed to the active side of the glove piece for a designated time interval, such as 1 and/or 5 minutes, at room temperature. At the end of the time exposure, both the glove material and the cover slip were dropped into a test tube containing 10 ml of neutralizing agent. Ten-fold dilutions were made in neutralizing solution. The dilutions were enumerated for surviving bacteria using standard agar plating method. Results were reported on a logarithmic scale. In general, a 2-log reduction against a broad spectrum of microorganisms is assessed as an anti-microbial effect.

EXAMPLES

Example 1

Example 1 demonstrated a hydrophilic polymer coating on an elastomeric article as a vehicle in which the antimicrobial agent was incorporated in order to control its release, thereby providing sustainable activity.

TABLE 3

| Materials: | | |
|---|---|---|
| Chemical Name | Trade Name | Manufacturer/Location |
| Benzalkonium Chloride | Benzalkonium Chloride (BKC) | Aldrich Chemical Co./ Milwaukee, WI |
| Chlorhexidine Gluconate | Chlorhexidine Gluconate (CHG) | Aldrich Chemical Co./ Milwaukee, WI |
| Methyl Methacrylate Copolymer Dispersion | Eudragit ® RS 30D | Degussa/Piscataway, NJ |
| Nonionic Paraffin Wax Emulsion | Michem ® Lube 743 (ML 743) | Michelman Inc./ Cincinnati, Ohio |
| Triethyl Citrate | Triethyl Citrate (TEC) | Aldrich Chemical Co./ Milwaukee, WI |
| Acetylenic Diol/ Alkylarylalkoxylate Surfactant | Surfynol ® TG | Air Products/Allentown, PA |
| Silicone Wetting Agent | BYK-348 | BYK-Chemie/ Wallingford, CT |

Wetting Composition: A 3% solution was prepared by adding 10 g of Surfynol® TG and 5 g of BYK-348 to 485 g of deionized water (DI water). The mixture was stirred for 20 min to achieve a solution containing 2% Surfynol® TG and 1% BYK-348.

BKC Solution: A 50% solution was prepared by adding 51.65 g of BKC to 103.3 g of DI water. The mixture was stirred for 1 h, until all foam dissipated and the solid completely dissolved.

Formulation 1-1 (antimicrobial): 4.57 g of wetting composition was added to a dipping tank containing 2268 g of DI water. 92.7 g of a 50% solution of BKC was added with continuous stirring. The mixture was stirred for 20 min until the foam dissipated. Then, a solution containing 115.3 g of CHG and 884.76 g of DI water was added slowly to the mixture. An additional amount of 1172.7 g of DI water was added to the solution. The mixture was continuously stirred for 30 min.

Formulation 1-2 (coating): 4.57 g of wetting composition was added to a dipping tank containing 2268 g of DI water. 90.83 g of a 50% solution of BKC was added with continuous stirring. The mixture was stirred for 20 min until the foam dissipated. Then, a solution containing 115.8 g of CHG and 884.76 g of DI water was added slowly to the solution. 181.51 g Eudragit® RS 30D, 142.07 g of ML 743, and 7.276 g of TEC were added to the mixture. Then, 841.18 g of DI water was added to the mixture and stirred for an additional 20 min. The resulting coating compositions contained the following ingredients and amounts:

TABLE 4

| Formulation 1-1 | Concentration (%) | Dry % | Amount (g) |
| --- | --- | --- | --- |
| BKC (50%) | 1.020 | 66.623 | 92.700 |
| CHG (20%) | 0.508 | 33.181 | 115.300 |
| Wetting composition (3%) | 0.003 | 0.196 | 4.570 |
| DI water | — | — | 4323.430 |
| Total | 1.531 | 100.000 | 4536.000 |

TABLE 5

| Formulation 1-2 | Concentration (%) | Dry % | Amount (g) |
| --- | --- | --- | --- |
| BKC (50%) | 1.000 | 25.806 | 90.830 |
| CHG (20%) | 0.510 | 13.161 | 115.800 |
| Wetting composition (3%) | 0.003 | 0.077 | 4.570 |
| Eudragit ® RS 30D (30%) | 1.200 | 30.968 | 181.510 |
| ML 743 (32%) | 1.002 | 25.858 | 142.070 |
| TEC | 0.160 | 4.129 | 7.276 |
| DI water | — | — | 3993.944 |
| Total | 3.875 | 100.000 | 4536.000 |

Glove Treatment: The nitrile gloves were subjected to a pre-treatment process prior to being treated. This process involved drying the nitrile gloves in the oven at 90° C. for 30 min. Then, the gloves were placed in a PE bag and cooled to room temperature in the desiccator (approximately 30 min).

For Sample 1-1 (control), following glove pre-treatment, the glove surface was treated using a dipping process. A nitrile glove was placed on a former, inverted and dipped into the antimicrobial formulation for 10 sec. While the former was still inverted, it was removed from the dipping tank and allowed to drip dry for 10 sec. The dipped glove was placed in the oven at 90° C. for 20 min. It was then removed from the oven and allowed to cool to room temperature (approximately 20 min).

For Sample 1-2 (coated), following the pre-treatment, the glove surface was treated with the same dipping process as the control glove, but using the coating formulation (formulation 1-2). The dipped glove was dried in the oven at 90° C. for 30 min. It was removed from the oven and allowed to cool to room temperature (approximately 30 min).

Glove Evaluation: Antimicrobial Agent Measurement by HPLC: Both Samples 1-1 and 1-2 were placed in a dispenser box (without desiccant) and aged in the oven for 7 days at 70° C. Using the HPLC method listed above, the coating concentrations for the coated glove are set forth in the following Table 6:

| | Coating Concentration (mg/glove) | | | |
| --- | --- | --- | --- | --- |
| | Water Extraction | | Methanol Extraction | |
| | BKC | CHG | BKC | CHG |
| Sample 1-1 (control) | | | | |
| Before Age | 1.2 ± 0.1 | 4.4 ± 0.8 | 6.7 ± 0.3 | 8.0 ± 1.0 |
| After Age | <0.02 | 0.17 ± 0.03 | N/A | N/A |
| Sample 1-2 (coated) | | | | |
| Before Age | 1.5 ± 0.1 | 3.7 ± 0.1 | 5.8 ± 0.1 | 7.6 ± 0.3 |
| After Age | 0.15 ± 0.03 | 1.5 ± 0.2 | N/A | N/A |

The measurements demonstrated that less than half of the antimicrobial agents remained on the surface of the glove after drying during glove treatment (before aging). It is believed that moisture accumulated during the drying and aging stages facilitated the migration of antimicrobial agent into the body of the glove. Marked improvement in antimicrobial availability was seen with the addition of a hydrophilic polymer in Formulation 1-2. Its use in Sample 1-2 resulted in greater retention of the antimicrobial agents on the surface when comparing before and after age results of the control and coated nitrile gloves.

Antimicrobial Activity: The antimicrobial activity of both Samples 1-1 and 1-2 was tested before and after aging against *P. aeruginosa* and MRSA with a 5 min exposure time:

TABLE 7

| Sample 1-1 | *P. aeruginosa* | MRSA |
| --- | --- | --- |
| Before Age | >5.64 | 3.75 |
| After Age | 0.18 | −0.04 |

TABLE 8

| Sample 1-2 | *P. aeruginosa* | MRSA |
| --- | --- | --- |
| Before Age | 3.44 | >5.15 |
| After Age | 1.29 | 2.33 |

The test results show that when both the hydrophilic polymer and the antimicrobial agents were combined in Formulation 1-2, higher antimicrobial activities were achieved after aging at 70° C. for 7 days. The availability of the antimicrobial agents was much greater in Sample 1-2 than in Sample 1-1 after aging. The polymer in Formulation 1-2 reduced migration of antimicrobial agent into the glove body and thus provided adequate surface concentration of antimicrobial agent.

Example 2

Coating Formulations and Glove Treatment: Formulation 2-1 consisted of a hydrophilic polymer (Eudragit® RS 30D), hydrophobic wax (ML 743), and antimicrobial agents (BKC and CHG). In Formulation 2-2, the hydrophobic wax was replaced with a conventional plasticizer (triethyl citrate, TEC). The formulations were prepared in a similar manner to Example 1. The resulting coating compositions contained the following ingredients and amounts:

TABLE 9

| Ingredients | Formulation 2-1 Dry % | Formulation 2-2 Dry % |
|---|---|---|
| BKC (50%) | 27.005 | 35.051 |
| CHG (20%) | 13.503 | 17.525 |
| Wetting composition (3%) | 0.081 | 0.105 |
| Eudragit ® RS 30D (30%) | 32.406 | 31.545 |
| ML 743 (32%) | 27.005 | — |
| TEC | — | 5.25 |
| Total | 100.000 | 100.000 |

Following glove pre-treatment, the glove samples were dipped using the same method described in Example 1, but dried at 70° C. for 20 minutes. The resulting nitrile gloves are labeled Samples 2-1 and 2-2. The nitrile gloves were packed in the aluminum pouch described in the Experimental introduction with one small and one large desiccant.

Antimicrobial Activity: The antimicrobial activity of the coating was tested before and after aging (70° C./6 days) against *P. aeruginosa* and MRSA using a 5 min exposure time. The dry coating weights (DCW) listed below were measured using the method described earlier.

TABLE 10

| Glove ID | Coating Formulation | DCW (mg/glove) | *P. aeruginosa* 0 day | *P. aeruginosa* Aged | MRSA (5 min) 0 day | MRSA (5 min) Aged |
|---|---|---|---|---|---|---|
| Sample 2-1 | 2-1 | 69.12 | >4.81 | 0.65 | >5.3 | 2.48 |
| Sample 2-2 | 2-2 | 69.57 | >5.62 | 0.53 | >4.83 | 1.73 |

The test results set forth in the table demonstrate that the hydrophobic wax in Sample 2-1 provided higher antimicrobial activities than the conventional plasticizer in Sample 2-2. While not wishing to be bound by theory, it is believed that the wax functioned as both a plasticizer and a hydrophobic component, assisting the hydrophilic polymer in the delivery of the antimicrobial agents to the surface of the glove.

Example 3

This example demonstrated that a coating containing specifically one antimicrobial agent, CHG, in combination with a hydrophilic polymer and a hydrophobic wax, was capable of exhibiting high antimicrobial activities with "quick kill" capabilities.

Coating Formulation and Glove Treatment: 4.53 g of wetting composition was added to a dipping tank containing 2268 g of DI water. Then, a solution containing 340.2 g of CHG and 659.8 g of DI water was added slowly to the solution and allowed to stir until the foam dissipated. 181.4 g Eudragit® RS 30D, 141.75 g of ML 743, and then 944.85 g of DI water was added to the mixture and stirred for an additional 20 min. The resulting coating composition contained the following ingredients and amounts:

TABLE 11

| Formulation 3-1 | Concentration (%) | Dry % | Amount (g) |
|---|---|---|---|
| CHG (20%) | 1.500 | 40.508 | 340.200 |
| Wetting composition (3%) | 0.003 | 0.081 | 4.530 |
| Eudragit ® RS 30D (30%) | 1.200 | 32.406 | 181.400 |
| ML 743 (32%) | 1.000 | 27.005 | 141.750 |
| DI Water | — | — | 3868.120 |
| Total | 3.703 | 100.000 | 4536.000 |

Nitrile exam gloves I and II ("I" and "II" denote different nitrile glove manufacturers) were dipped in a similar manner as those in Example 1. They were dried at 70° C. for 20 min and then cooled to room temperature. The resulting gloves are labeled Samples 3-1 and 3-2, respectively. These gloves were packaged in the aluminum pouch described in the Experimental introduction with two small and two large desiccants.

Antimicrobial Activity: Using the method described earlier, the antimicrobial activity of the coating was tested before and after aging (70° C./7 days) against *P. aeruginosa* and MRSA at both 1 min and at 5 min exposure times. The dry coating weight (DCW) was measured using the method listed above.

TABLE 12

| Glove ID | DCW (mg/glove) | Before Age/5 min *P. aerugi-nosa* | Before Age/5 min MRSA | After Age *P. aeruginosa* 1 min | After Age *P. aeruginosa* 5 min | After Age MRSA 1 min | After Age MRSA 5 min |
|---|---|---|---|---|---|---|---|
| Sample 3-1 | 43.9 | >5.26 | >5.13 | N/A | 2.81 | N/A | 2.91 |
| Sample 3-2 | 45.9 | N/A | N/A | 2.82 | 4.35 | 1.35 | >5.34 |

A "quick kill" was achieved when using the sole antimicrobial agent, CHG, in combination with the coating comprising a hydrophilic polymer and a hydrophobic wax.

Example 4

This example demonstrated the antimicrobial efficacy of elastomeric articles treated with a coating according to the invention.

Coating Formulation and Glove Treatment: Using Coating Formulation 3-1, nitrile exam gloves were dipped in a manner similar to Example 1, but dried at 70° C. for 20 min and cooled to room temperature. The nitrile gloves were packaged according to Example 3. After 70° C./7 days' aging, the glove activity was tested immediately after pouch package was opened. A second test was performed after 4 weeks of storage at ambient conditions in the opened pouch package (called Open Pouch test). The resulting nitrile gloves are labeled Samples 4-1 and 4-2, respectively.

Antimicrobial Activity: Using the method described earlier, the nitrile gloves of this example were tested at both one and five minutes exposure time:

TABLE 13

| Glove ID | Age | *P. aeruginosa* 1 min | *P. aeruginosa* 5 min | MRSA 1 min | MRSA 5 min |
|---|---|---|---|---|---|
| Sample 4-1 | 70° C./7 days | 2.82 | >4.91 | >5.02 | >5.02 |
| Sample 4-2 | 70° C./7 days plus 4 weeks Open Pouch | 3.84 | 4.46 | 4.44 | >4.89 |

The test data show that surface treatment of antimicrobial coating in accordance with the present invention provided nitrile gloves with sustainable antimicrobial activity. With a moisture-resistant package, more than 2 log reduction at one minute exposure time against *P. aeruginosa* and MRSA was achieved, indicating "quick-kill" antimicrobial properties for Samples 4-1 and 4-2.

Example 5

Coating Formulation and Glove Treatment: Unless indicated otherwise, coating formulations were made in the same manner described in Example 3, comprising Eudragit® RS 30D, ML 743, CHG and wetting composition. Three separate batches of nitrile gloves were treated in order to test coating formulation and process replication. Dry coating weights were in the range of 45-50 mg/glove. The gloves are labeled as Samples 5-1, 5-2, and 5-3. The gloves were packaged in a similar manner to the method according to Example 3.

Antimicrobial Activity: Using the method described earlier, the antimicrobial activity of the nitrile gloves was tested on five minutes exposure time before and after age (70° C./7 days) against an array of bacteria including gram positives (*S. aureus* and *E. faecalis*), gram negative (*E. coli*, *P. aeruginosa* and *S. epidermidis*) and antibiotic resistant strains (VRE and MRSA):

TABLE 14

| | (after age) | | | |
|---|---|---|---|---|
| Glove ID | DCW (mg/glove) | S. aureus | E. coli | E. faecalis |
| Sample 5-1 | 49.0 | 4.47 | 4.94 | 4.29 |
| Sample 5-2 | 46.4 | 3.70 | 4.16 | 2.20 |
| Sample 5-3 | 47.1 | 4.44 | 4.78 | 3.14 |
| Glove ID | S. epidermidis | VRE | P. aeruginosa | MRSA |
| Sample 5-1 | 5.24 | 4.17 | 4.91 | 5.02 |
| Sample 5-2 | N/A | 2.27 | 3.79 | 4.09 |
| Sample 5-3 | 3.55 | 3.36 | 2.29 | 5.24 |

The test data demonstrated that the antimicrobial coating formulation according to the invention provided treated nitrile gloves with sustainable antimicrobial activities against a broad spectrum of microorganisms in a reliable and reproducible manner.

Example 6

The purpose of this study was to demonstrate instant and persistent kill of microorganisms provided by the antimicrobial glove of the invention in combination with an alcohol gel.

Alcohol gel, as a general antimicrobial agent, is commonly used for instant elimination of microorganisms, but is not considered sufficient by itself for preparation for surgical procedures. Therefore, it is standard practice before donning surgical gloves for surgeons to scrub their hands with a surgical scrub product, which normally contains an antimicrobial agent such as CHG. However, use of a surgical scrub can cause skin irritation and dryness over time.

Surgical gloves coated with the novel antimicrobial coating can be used in combination with common hand antiseptic alcohol gel to replace in part or in total the activity of pre-glove-donning hand scrubbing during preparation for surgery as a method of reducing infection. By pre-glove-donning hand scrubbing is meant the standard practice among surgeons of scrubbing their hands with a surgical scrub product which normally contains an antimicrobial agent prior to donning surgical gloves.

The surgical gloves used in this study were polyisoprene gloves commercially available from Cardinal Health, Inc., Dublin, Ohio, under the trade name Esteem SMT®. The hand antiseptic alcohol gel used in this study was commercially available from Cardinal Health, Inc., Dublin Ohio, under the trade name Biosoft®.

Coating Formulation and Glove Treatment: 4.53 g of wetting composition was added to a dipping tank containing 2401 g of DI water. Then, 1020.45 g of CHG was slowly added and allowed to stir until foam dissipated. A solution of 544.24 g of Eudragit® RS30D and 400 mL of water was slowly added. Following this, a solution containing 425.19 g of ML743 and 500 mL of DI water was added. Then, 1507.59 g DI water was added and stirred for an additional 30 min. The resulting coating composition contained the following ingredients and amounts:

TABLE 15

| Coating Formulation 6-1 | Concentration (%) | Dry % | Amount (g) |
|---|---|---|---|
| CHG (20%) | 3.000 | 40.530 | 1020.450 |
| Wetting Agent (3%) | 0.002 | 0.027 | 4.530 |
| Eudragit ® RS 30D (30%) | 2.400 | 32.424 | 544.240 |
| ML 743 (32%) | 2.000 | 27.020 | 425.190 |
| DI Water | — | — | 4808.590 |
| Total | 7.402 | 100.000 | 6803.000 |

Polyisoprene surgical gloves were inverted with the donning side being dipped in a similar manner to those specified in Example 1, dried at 70° C. for 20 min and cooled to room temperature. Both uncoated (Sample 6-1) and coated gloves (Sample 6-2) were packaged in accordance with conventional techniques and equipment. Subsequently, they were subjected to conventional gamma sterilization.

Antimicrobial Activity: The microbial suspension was prepared using the Direct Colony Method in sterile saline (Reference: *Methods for Dilution Antimicrobial Susceptibility Tests for Bacteria That Grow Aerobically*; Standard: M7-A6. Clinical and Laboratory Standards Institute). An aliquot of 0.2 ml of microbial suspension was added and spread over the agar surface of a petri dish and allowed to dry for 20 min. Then, 0.5 mL of Biosoft® was added and spread over the bacteria. Testing samples, approximately 56.72 cm$^2$, were cut from the palm areas of the surgical gloves and the active side was firmly placed in contact with the agar surface for a designated time interval. At the end of the time exposure, the microbial residue from the agar plate was rinsed twice with 5 ml of neutralizing solution total and transferred into 25 mL of neutralizing agent. Neutralizing agent containing the surviving microorganisms was enumerated for living bacteria using standard agar plating methods. Three parallel studies were conducted for each data point. The antimicrobial activity of sterilized Samples 6-1 and 6-2 were tested for both one-minute and six hours before and after aging (70° C./7 days) against *P. aeruginosa*, as seen in the table listed below:

TABLE 16

| Experiment | Glove ID | Alcohol Treatment | Sterilized/Before Age | | Sterilized/After Age | |
|---|---|---|---|---|---|---|
| | | | 1 min | 6 h | 1 min | 6 h |
| 1 | Sample 6-1 | With Alcohol | 3.45 | 0.69 | 2.81 | 2.36 |
| 2 | Sample 6-2 | Without Alcohol | 0.5 | 3.45 | 0.29 | 1.69 |
| 3 | Sample 6-2 | With Alcohol | 3.45 | 3.45 | 2.46 | 2.71 |

The combination of the alcohol gel and glove coated with the novel coating of the invention, Experiment 3, was able to maintain a higher antimicrobial activity than the uncoated glove combination, Experiment 1. The glove user would be provided with a controlled and extended release of CHG to the skin, thereby rendering persistent kill improving antimicrobial efficacy of CHG against various bacteria. Thus, the test data demonstrated that in combination with alcohol gel the surgical glove coated with the novel antimicrobial coating of the invention provided the glove user with a sustained protection of up to six hours.

Example 7

This example demonstrated the process of manufacturing the antimicrobial coating of the invention on the glove.

Coating Formulation and Glove Treatment: Prior to being treated, the nitrile gloves were subjected to a pre-treatment process, i.e. tumbling the nitrile gloves for 5 min at 70° C. Using Coating Formulation 3-1, 1000 nitrile exam gloves were sprayed for 225 sec and air-dried for 2 min. This process was repeated twice (three spraying intervals total). The treated nitrile exam gloves that were dried at 70° C. for 45 min and stored for 3 days before packaging are referred to as sample 7-1. Treated nitrile exam gloves that were dried at 70° C. for 30 min and stored for 1 day are referred to as sample 7-2. Then, samples 7-1 and 7-2 were cooled to ambient conditions for 15 min. They were packaged using the same conditions listed in Example 3.

Dry Coating Weight (DCW): The dry coating weight was determined using the following process. First, ten treated and ten untreated gloves were pre-dried in a forced-air oven at 75° C. for 30 min. Next, the gloves were placed in a desiccator to cool for 30 min. The weights of the untreated and treated gloves were measured before washing. Then, the gloves were tied with rubber bands to prevent water from going inside the glove. Together, they were washed/tumbled rigorously under continuous flow of tap water in a 5L container for 2.5 min. The water was removed and the washing process was repeated three more times. Any remaining water was squeezed out from the gloves, before the gloves were untied. Finally, the gloves were dried in the oven at 80° C. for 30 min. The weights of the untreated and treated gloves after washing were measured. The total extractable materials for the gloves were determined by taking the difference between weights of gloves before and after washing. The DCW was determined by taking the difference between the total extractable materials of the treated and untreated gloves.

Antimicrobial Activity: The antimicrobial activity of the gloves was tested for both one and five minutes exposure times after aging (70° C./7 days) against a broad spectrum of gram positive and gram negative bacteria as seen in the table listed below:

TABLE 17

One-Minute Exposure Time

| Aged Sample | DCW (mg/glove) | St. aureus | E. coli | E. faecalis | S. epiderm | VRE | P. aeruginosa | MRSA |
|---|---|---|---|---|---|---|---|---|
| Sample 7-1 | 53 | 4.49 | 5.62 | 3.99 | 4.42 | 3.59 | 2.79 | 5.40 |
| Sample 7-2 | 47 | 5.18 | 5.62 | 4.73 | 5.06 | 5.02 | 3.70 | 5.30 |

TABLE 18

Five-Minute Exposure Time

| Aged Sample | DCW (mg/glove) | St. aureus | E. coli | E. faecalis | S. epiderm | VRE | P. aeruginosa | MRSA |
|---|---|---|---|---|---|---|---|---|
| Sample 7-1 | 53 | 5.18 | 5.62 | 4.85 | 5.00 | 4.82 | 4.52 | 5.40 |
| Sample 7-2 | 47 | 5.18 | 5.62 | 5.11 | 5.16 | 4.73 | 5.34 | 5.40 |

The test data clearly showed that the novel antimicrobial coating of the invention can be applied to a large amount of gloves on a manufacturing scale and the resultant gloves provided antimicrobial properties against a broad spectrum of microorganisms as obtained in the lab.

The invention has been described herein above with reference to various and specific embodiments and techniques. It will be understood, however, that reasonable modifications of such embodiments and techniques can be made without substantially departing from either the spirit or scope of the invention defined by the following claims.

The invention claimed is:

1. An article comprising a glove having an inside hand-contacting surface and an outside surface, and a surface coating provided at least on the outside surface, wherein the surface coating comprises:
   a hydrophilic film-forming polymer,
   a nonionic paraffin wax dispersion wherein the carbon chain length of the wax is 25-30 carbon,
   and a non-volatile water-soluble antimicrobial agent,
   wherein the article is essentially free of starch and powder.

2. The article according to claim 1, wherein the glove is selected from the group consisting of a food-contact glove, a dental glove, an industrial glove, a laboratory glove and a medical glove.

3. The article according to claim 2, wherein the medical glove is selected from the group consisting of an exam glove and a surgical glove.

4. The article according to claim 1, wherein the article contains less than about 2 mg of starch and powder combined.

5. The article according to claim 1, wherein the glove comprises an elastomer selected from the group consisting of natural rubber latex, nitrile, polychloroprene, 2-chloro-1,3-butadiene, 2,3-dichloro-1,3-butadiene, polybutadiene, polyvinylchloride, polyurethane, synthetic polyisoprene, neoprene, styrene diblock copolymers, styrene triblock copolymers, graft copolymers and blends thereof.

6. The article according to claim 5, wherein the elastomer is nitrile.

7. The article according to claim 1, wherein the hydrophilic film-forming polymer is selected from the group consisting of collagen, chitosan, gum, carrageenan, pullulan, pectin, dextrin, quince, hyaluronic acid, chondroitin sulfate, methyl polyglutamate, sodium alginate, polyacrylic acid, polymethyl acrylate, polybutyl acrylate, polyacrylamide, poly N-isopropyl acrylamide, ammonium polyacrylate, crosslinked sodium polyacrylate, acrylic or methacrylic copolymer, methyl cellulose, ethyl cellulose, cationized cellulose, carboxymethyl cellulose, hydroxyethyl cellulose, hydroxypropyl methyl cellulose, polyvinyl caprolactam, olefin-maleic anhydride copolymer, isobutylene-sodium maleic anhydride copolymer, ethylene-maleic anhydride copolymer, vinylpyrrolidone-styrene copolymer, vinylpyrrolidone-vinyl acetate copolymer, diethyl sulfate vinylpyrrolidone-dimethylaminoethyl-methacrylic acid copolymer, polymethacryloyloxyethyltrimethyl ammonium chloride, carboxylic vinyl polymer, alkyl vinyl etherimaleic anhydride copolymer, zwitterionic polymer, polyvinyl methyl ether, toluene sulfonamide polymer, polyurethane, polyamide epichlorohydrin, polyethylene-imine, polyethylene glycol, polyvinyl alcohol and mixtures thereof.

8. The article according to claim 7, wherein the hydrophilic film-forming polymer is a cationic acrylic copolymer of acrylic acid and methacrylic ester with quaternary ammonium groups.

9. The article according to claim 1, wherein the surface coating further comprises a hydrophobic component selected from the group consisting of a non-volatile coalescing solvent, waxy compound, alkyl cellulose, oligomeric polyethylene, magnesium stearate, diethyl phthalate, tributyl citrate, polybutylene, dibutyl phthalate, anionic protein, shellac, sugar, glycol, polyol, disaccharide, triacetyl citrate, polysorbate 80, triacetine, triethyl citrate, paraffin wax, synthetic wax, polyethylene wax, oxidized polyethylene wax, ethylene acrylic acid copolymer wax, ethylene vinylacetate copolymer wax, silicone wax, fluoroethylene wax, carnauba wax, Fischer-Tropsch wax, ester wax and combinations thereof.

10. The article according to claim 9, wherein the hydrophobic component is a paraffin wax.

11. The article according to claim 1, wherein the non-volatile water-soluble antimicrobial agent is selected from the group consisting of 1,1'-hexamethylene, hexamethylene biguanide hydrochloride, polyhexamethylene biguanide hydrochloride, chlorhexidine, 2-amino-2-methyl-1-propanol, benzalkonium chloride, chloroallyl hexaminium chloride, benzethonium chloride, methylbenzethonium chloride, cetyl trimethyl ammonium bromide, didecyldimethyl ammonium chloride, cetyl pyridinium chloride and mixtures thereof.

12. The article according to claim 1, wherein the non-volatile water-soluble antimicrobial agent is chlorhexidine digluconate.

13. The article according to claim 11, wherein the water-soluble antimicrobial agent is a combination of chlorhexidine digluconate and benzalkonium chloride.

14. The article according to claim 1, wherein the article provides antimicrobial activity following storage open to the atmosphere at ambient conditions for at least about 1 week, wherein antimicrobial activity is measured as 2-log reduction against a broad spectrum of microorganisms.

15. The article according to claim 1, wherein the article provides antimicrobial activity following storage according to ASTM D 6319-00a$^{\epsilon 3}$, Test Method D 573, wherein antimicrobial activity is measured as 2-log reduction against a broad spectrum of microorganisms.

16. The article according to claim 1, wherein the glove is a surgical or examination glove with less than about 2 mg of starch and powder combined, wherein the surface coating comprises a cationic acrylic copolymer of acrylic acid and methacrylic ester with quaternary ammonium groups as the hydrophilic film-forming polymer, a non-ionic paraffin wax dispersion wherein the carbon chain length of the paraffin wax is 25-30 carbons and a combination of chlorhexidine digluconate and benzalkonium chloride as the non-volatile water-soluble antimicrobial agent.

17. The article according to claim 16, wherein the chlorhexidine gluconate is present in an amount ranging from about 5.0% to about 60.0% by weight of total solids in the surface coating, the benzalkonium chloride is present in an amount ranging from more than 0.0% to about 33.0% by weight of total solids in the surface coating, the hydrophilic polymer is present in an amount ranging from about 2.0% to about 60.0% by weight of total solids in the surface coating and the non-ionic paraffin wax dispersion wherein the carbon chain length of the paraffin wax is 25-30 carbons is present in an amount ranging from about 1.5% to about 40.0% by weight of total solids in the surface coating, and the dry coating weight of the surface coating is between about 20 to about 100 mg total solids per glove.

18. The article according to claim 17, wherein the dry coating weight is between about 40 to about 50 mg total solids per glove.

19. The article according to claim 1, wherein the article has an antimicrobial effect following about five minutes of exposure to two or more of the microorganisms selected from the group consisting of *Staphylococcus aureus, Enterococcus faecalis, Escherichia coli, Pseudomonas aerignosa*, methicillin-resistant *Staphylococcus aureus* (MRSA) and vancomycin-resistant *Enterococcus faecium* (VRE).

20. The article according to claim 1, wherein the article has an antimicrobial effect following about one minute of exposure to two or more of the microorganisms selected from the group consisting of *Staphylococcus aureus, Enterococcus faecalis, Escherichia coli, Pseudomonas aerignosa*, methicillin-resistant *Staphylococcus aureus* (MRSA) and vancomycin-resistant *Enterococcus faecium* (VRE).

* * * * *